United States Patent
Baumann et al.

(10) Patent No.: US 9,538,983 B2
(45) Date of Patent: Jan. 10, 2017

(54) DEVICE FOR GUIDING A MEDICAL IMAGING PROBE AND METHOD FOR GUIDING SUCH A PROBE

(71) Applicant: KOELIS, Grenoble (FR)

(72) Inventors: Michael Baumann, Grenoble (FR); Antoine Leroy, Meylan (FR)

(73) Assignee: KOELIS, Grenoble (FR)

(*) Notice: Subject to any disclaimer, the term of this patent is extended or adjusted under 35 U.S.C. 154(b) by 0 days.

(21) Appl. No.: 14/397,407

(22) PCT Filed: Jun. 3, 2013

(86) PCT No.: PCT/EP2013/061382
§ 371 (c)(1),
(2) Date: Oct. 27, 2014

(87) PCT Pub. No.: WO2013/178823
PCT Pub. Date: Dec. 5, 2013

(65) Prior Publication Data
US 2015/0119715 A1    Apr. 30, 2015

(30) Foreign Application Priority Data
Jun. 1, 2012 (FR) ...................... 12 55130

(51) Int. Cl.
*A61B 5/05* (2006.01)
*A61B 8/00* (2006.01)
(Continued)

(52) U.S. Cl.
CPC .......... *A61B 8/4254* (2013.01); *A61B 8/0841* (2013.01); *A61B 8/12* (2013.01); *A61B 8/4461* (2013.01);
(Continued)

(58) Field of Classification Search
CPC ............. A61B 8/12; A61B 8/145; A61B 8/08; A61B 8/4488; A61B 5/06
See application file for complete search history.

(56) References Cited

U.S. PATENT DOCUMENTS 6,045,508 A    4/2000  Hossack et al.
6,248,074 B1   6/2001  Ohno et al.
(Continued)

FOREIGN PATENT DOCUMENTS

FR    2 920 961 A1    3/2009
JP    2011-104108 A   6/2011
(Continued)

OTHER PUBLICATIONS

International Search Report of PCT/EP2013/061382 dated Aug. 28, 2013.

Primary Examiner — Joel Lamprecht
(74) Attorney, Agent, or Firm — Sughrue Mion, PLLC

(57) ABSTRACT

A device for guiding a medical imaging probe in order to move the probe close to an anatomical space, the probe having a mechanism for acquiring images of the anatomical space, and the device having at least one sensor mounted to the probe. The device includes a processing mechanism for deducing a rotation of the probe in the space from the signals generated by the sensor and for estimating a plurality of plausible positions of the probe relative to the anatomical space by deducing the rotation of the probe in the space. The processing mechanism is arranged such as to determine the position of the probe relative to the anatomical space from the plausible positions. Also disclosed is a method for guiding the probe.

14 Claims, 3 Drawing Sheets

(51) Int. Cl.
*A61B 8/12* (2006.01)
*A61B 17/34* (2006.01)
*A61B 8/08* (2006.01)
*A61B 17/00* (2006.01)

(52) U.S. Cl.
CPC .......... *A61B 8/4488* (2013.01); *A61B 8/5215* (2013.01); *A61B 17/3403* (2013.01); *A61B 34/20* (2016.02); *A61B 2017/00274* (2013.01); *A61B 2017/3405* (2013.01); *A61B 2017/3413* (2013.01); *A61B 2034/2048* (2016.02); *A61B 2090/3784* (2016.02)

(56) References Cited

U.S. PATENT DOCUMENTS

2007/0197896 A1* 8/2007 Moll .................. A61B 1/00039
                                                          600/407
2008/0262356 A1  10/2008 Chalana et al.
2009/0306509 A1  12/2009 Pedersen et al.
2011/0081063 A1   4/2011 Leroy et al.
2011/0184684 A1   7/2011 Li et al.

FOREIGN PATENT DOCUMENTS

WO    2011/094585 A1    8/2011
WO    2011/161684 A2   12/2011

* cited by examiner

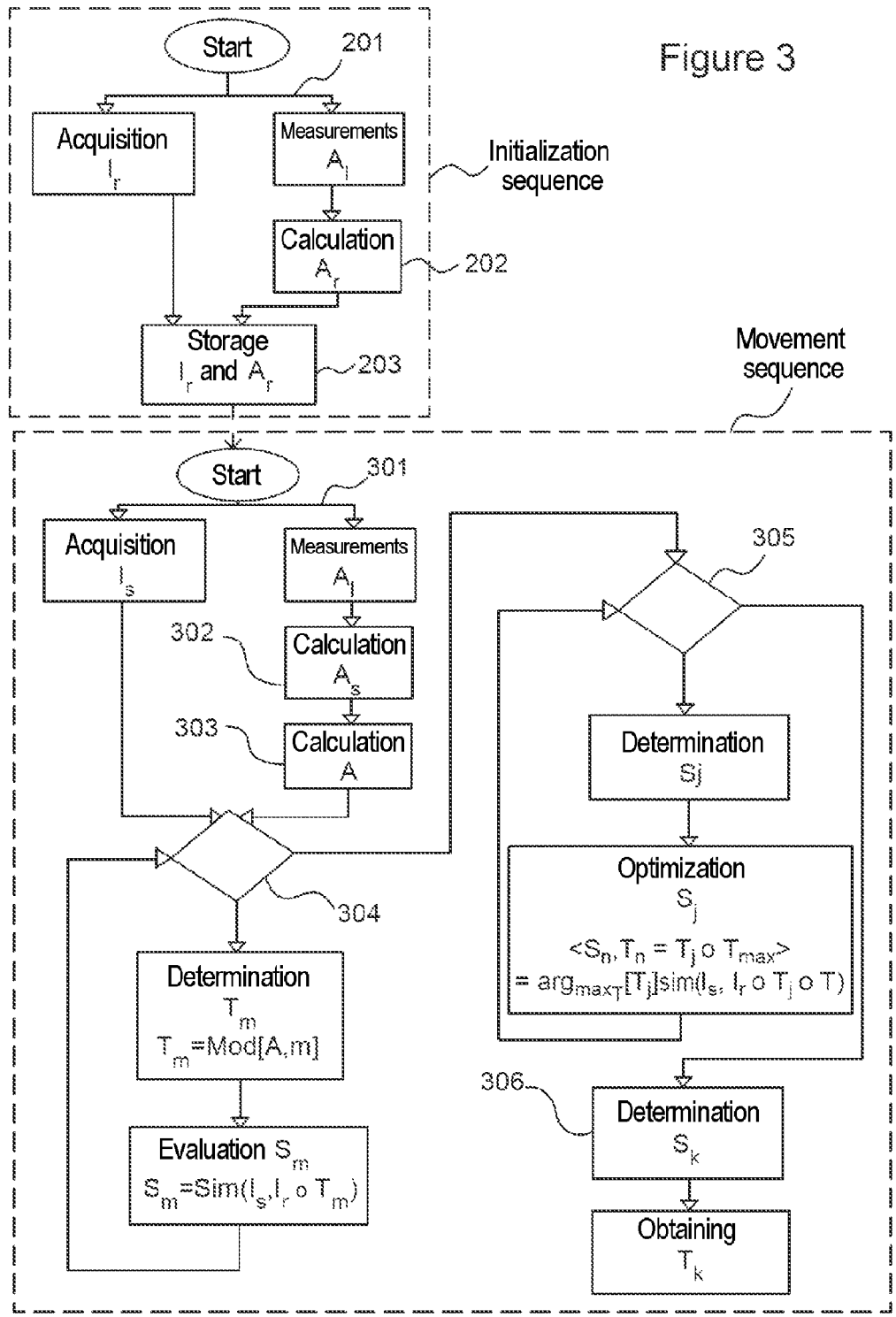

DEVICE FOR GUIDING A MEDICAL IMAGING PROBE AND METHOD FOR GUIDING SUCH A PROBE

CROSS-REFERENCE TO RELATED APPLICATIONS

This is a National Stage of International Application No. PCT/EP2013/061382 filed Jun. 3, 2013, claiming priority based on French Patent Application No. 12 55130 filed Jun. 1, 2012, the contents of all of which are incorporated herein by reference in their entirety.

The invention relates to a device for guiding a medical imaging probe and to a method for guiding such a probe.

BACKGROUND OF THE INVENTION

So-called "open" operations may prove stressful for a patient. Thus, practitioners are resorting more and more to so-called "minimally invasive" operations, during which medical instruments are inserted through the skin (percutaneously), or into a natural passage of the patient (vagina, rectum, auditory canal, etc.), or into an artificial passage connected to the body of the patient (cannula, artificial vein, trocar, etc.). To this end, practitioners are assisted by images of the organ or organs in question, the images being taken before or during the intervention.

In urology, in order to detect a possible prostate cancer, it is known to carry out a prostate biopsy. This involves taking tissue samples from the prostate itself, said samples subsequently being analyzed in a laboratory in order to detect the presence of possible cancer cells. To this end, the patient is laid on his side or on his back. In the case of a transrectal biopsy, a medical instrument comprising a needle holder holding a biopsy needle is inserted into the natural passage, namely the rectum. By using the medical instrument, the clinician pierces the wall of the colon to reach the prostate and thus take prostate tissue samples. For the sampling, a two-dimensional ultrasound scan of the prostate, taken during the intervention in the form of a stream of images, is typically used by the clinician in order to position the needle relative to the prostate. However, the use of a two-dimensional image to carry out three-dimensional positioning, the relatively indiscriminate nature of an ultrasound scan as well as the rather symmetrical shape of the prostate and its mobility often lead to a significant positioning error of the needle relative to the prostate, so that the samples cannot in fact be taken regularly or in a targeted fashion, depending on the approach.

In order to help the clinician take the tissue samples at the appropriate positions, there are numerous devices for guiding the medical instrument.

For example, guide devices comprising an articulated arm controlled in order to move the proximal end of the instrument are known. The position of the proximal end in the reference frame of the fixed base of the articulated arm can therefore always be determined. Knowing the position of the prostate in the reference frame, it is thus possible to know the position of the instrument relative to the prostate throughout the intervention.

However, such a guide device is particularly bulky.

Moreover, such a guide device only takes into account the movements of the instrument. However, the patient may also shift during the intervention, which leads to movement of the prostate. For example, the patient may not be under local anesthetic and/or he may not be restrained, so that he can shift to find a more comfortable position, or simply by reflex. Merely the muscle activity of the patient, such as his respiratory cycle, may also cause the prostate to move. Furthermore, the prostate is a soft organ, so that the pressure of the instrument, or even merely the contact of the needle, without its being inserted into the prostate, is sufficient to move said prostate. In addition, the bladder fills and enlarges during the intervention. It may therefore press on the prostate so as to move the latter. Hematomas, or liquid accumulations, caused or not caused by the intervention, may also occur and cause movement of the prostate.

Thus, even if the position of the instrument in the reference frame is correctly determined, the prostate may shift so that the clinician cannot reach the initially intended region with the needle.

Guide devices comprising one or more transmitters (or markers) fixed to the instrument and a receiver (or detector of the markers), which is arranged in the room in which the patient is, are also known. For example, the transmitters generate induced currents which the receiver can detect, which makes it possible to position the transmitters, and therefore the instrument, in the reference frame of the receiver. Knowing the position of the prostate in the reference frame of the receiver, it is thus possible to know the position of the instrument relative to the prostate during the intervention.

In the same way, however, such a guide device is bulky and takes into account only the movements of the instrument, and in no way the possible movements of the prostate: the position of the prostate relative to the instrument is in fact rapidly displaced, and therefore lost. In other cases, it is possible to add additional sensors on an anatomical volume targeted by an intervention, in order to resolve this problem, but this invasive solution is not applicable to an intervention on the prostate, which is a soft internal organ.

Recently, a new class of guide devices has appeared, allowing the clinician to carry out punctures in the prostate more precisely. Specifically, said guide devices comprise an ultrasound probe provided with means for three-dimensional image acquisition. Said probe is arranged in the guide device in such a way that a position of the probe relative to the instrument is known, or at least can always be determined. For example, the probe is fixed to the instrument.

The probe therefore continuously provides images of the natural passage, the surrounding tissue and the prostate during the movement of the instrument in the natural passage. These images are then processed in order to determine the position of the probe, and therefore of the instrument, with respect to the prostate. Since the images contain information about the movements of the prostate, the guiding of the instrument is more precise. Patent Application FR 2 920 961 describes such a guide device.

However, ultrasound probes acquiring images in three dimensions present the drawback of requiring several seconds for the acquisition of an image. Furthermore, since the three-dimensional images contain a large amount of information, the processing of said images consequently also takes a few seconds. It is therefore not possible to know the position of the probe relative to the prostate rapidly enough after the start of the acquisition of a new image, so that the positioning of the instrument relative to the prostate still remains too imprecise. In addition, this approach lengthens the duration of the intervention.

In order to overcome the aforementioned drawbacks, a third class of guide devices is known, combining localization of the instrument with the images taken by an ultrasound probe (two dimensions, three dimensions, etc.) and localization by a transmitter/receiver assembly.

The transmitter/receiver assembly makes it possible to rapidly provide an approximate position of the probe, and therefore of the instrument, relative to the prostate. This position is used to initialize the processing of the images provided by the probe, the processing of the images then making it possible to refine the position of the probe relative to the prostate.

Thus, the position of the probe, and therefore of the instrument, relative to the prostate is adjusted around an overall position determined rapidly by the transmitter/receiver system.

Such a guide device makes it possible to localize the probe, and therefore the instrument, very precisely relative to the prostate, but requires both a probe/image-processing system and a transmitter/receiver system. In addition, the receiver is often bulky. Furthermore, external perturbations such as magnetic interference may hamper the localization of the receivers.

It has therefore been envisioned to replace the transmitter/receiver system with a sensor carried by the ultrasound probe.

However, such devices prove unreliable, particularly in the event of large movements of the prostate between the capture of a reference image and of a subsequent monitoring image. This is because, with such devices, the processing of the images makes it possible to refine the position provided by the sensor only with local optimization methods. However, if the organ moves significantly because the patient shifts during the intervention, the position provided by the sensor may lie outside what is referred to as the "capture range" of the intended solution (i.e. the actual position of the probe relative to the prostate) and it then becomes impossible for a local optimization calculation to reach this solution. In this case, these devices then perform as poorly as the guide devices comprising only a single sensor, since they can provide extremely erroneous and possibly dangerous positions. Furthermore, it proves necessary to calibrate the guide device regularly in order to reset it to a position which is known relative to the prostate, which is time-consuming and onerous for the operator.

OBJECT OF THE INVENTION

It is an object of the invention to at least partly obviate the aforementioned drawbacks.

BRIEF DESCRIPTION OF THE INVENTION

To this end, a device is provided for guiding a medical imaging probe in order to bring said probe in proximity to an anatomical volume, the probe comprising means for acquiring images of the anatomical volume, the device comprising at least one sensor fixed to the probe and capable of generating signals representing at least one rotation of the probe in space. According to the invention, the device comprises a control unit which is connected to the probe and comprises means for processing the images in order to localize the probe relative to the anatomical volume, the processing means being capable of deducing a rotation of the probe in space on the basis of the signals generated by the sensor, and comprising means for estimating a plurality of plausible positions of the probe relative to the anatomical volume on the basis of at least the deduction of the rotation of the probe in space, the processing means being arranged in order to determine the position of the probe relative to the anatomical volume on the basis of a reference image of the anatomical volume, of at least one image acquired by the image acquisition means and the plausible positions.

Thus, the sensor provides signals making it possible to deduce rapidly at least one rotation of the probe in space. This rotation is used to initialize the calculation for determining one or more plausible positions of the probe relative to the anatomical volume in question. These plausible positions are then in turn used to initialize the processing of the images provided by the acquisition means, which makes it possible to determine the position of the probe relative to the anatomical volume. The estimation of the rotation in space therefore ultimately makes it possible to initialize, by calculating the plausible positions, the processing of the images provided by the acquisition means.

By providing this rotation of the probe in space, the processing of the images is made more robust since it is no longer necessary to determine the rotation of the probe in space on the basis of the images. Consequently, the processing of the images requires less information from the acquisition means in order to determine the full position of the probe relative to the anatomical volume. It therefore becomes possible to work with a smaller amount of information from the image acquisition means, which makes it possible to reduce the time taken for the acquisition of the images, and also to shorten the actual processing of the images. By virtue of the invention, the position of the probe relative to the anatomical volume is thus known precisely and rapidly, while obviating a bulky system of the transmitter/receiver type of the prior art, despite the possible movements of the anatomical volume.

Another advantage of the invention is therefore that a smaller amount of information from the acquisition means is necessary compared with guide devices of the prior art, based only on processing of the images in order to estimate the position of the probe relative to the anatomical volume in question. This makes it possible to speed up the process of image acquisition by the image acquisition means, and consequently to know the position of the probe relative to the anatomical volume sufficiently rapidly after the start of the acquisition of a new image, so that the positioning of the probe relative to the prostate is precise.

Thus, the combination of a sensor generating signals representing a partial position of the probe, image processing means and estimation means makes it possible both to obtain rapid monitoring of the position of the probe relative to the anatomical volume, by virtue of the sensor, and at the same time to obtain reliable monitoring of said position even in the event of significant shifts of the targeted anatomical volume, by virtue of the image estimation means.

Estimating the plausible positions of the probe relative to the anatomical volume on the basis of information about the position of the probe in space, provided by the sensor, makes it possible to limit the processing of the images and avoid situations in which the processing of the images does not make it possible to obtain the real position of the probe relative to the anatomical volume, as with certain devices of the prior art.

According to a preferred embodiment, the sensor is capable of generating only signals representing the rotation of the probe in space.

Thus, the estimation means determine the plausible positions of the probe relative to the anatomical volume only on the basis of information about the rotation of the probe in space, i.e. without information about the translation of the probe in space. When a patient is lying down during the intervention, it is quite likely that he will shift by a few centimeters on his bed, but it is far less likely that the anatomical volume will turn by more than a few degrees. By virtue of this embodiment, only information relating to the rotation of the probe is used, i.e. the information which has less likelihood of being greatly modified during the intervention. The estimation means then make it possible to estimate the plausible positions of the probe with respect to the anatomical volume, and therefore to estimate the translations of the probe in space, which have a high probability of corresponding to the real position of the probe relative to the anatomical volume.

Here, an anatomical volume is intended to mean both an organ such as the kidney, the breast, the uterus, the thyroid, the liver or the prostate, and a cavity, for example the Douglas' cul-de-sac.

The invention also relates to a method for guiding a medical probe for medical imaging in order to bring the probe in proximity to an anatomical volume, the probe comprising means for acquiring images of the anatomical volume, and the method comprising the step of fixing to the probe at least one sensor capable of generating signals representing at least one rotation of the probe in space. According to the invention, the method comprises the steps of:

processing the signals generated by the sensor in order to deduce therefrom at least one rotation of the probe in space, estimating a plurality of plausible positions of the probe relative to the anatomical volume on the basis of at least the deduction of the rotation of the probe in space, processing the images in order to localize the probe relative to the anatomical volume by determining the position of the probe relative to the anatomical volume on the basis of a reference image of the anatomical volume, of at least one image acquired by the image acquisition means, and of the plausible positions which have been determined.

BRIEF DESCRIPTION OF THE DRAWINGS

The invention will be understood more clearly in the light of the following description of a nonlimiting particular embodiment of the invention. Reference is made to the appended figures, in which:

FIG. 3 is a diagram illustrating the various steps of a particular embodiment of the method for guiding a probe of the device illustrated in FIG. 1.

DETAILED DESCRIPTION OF THE INVENTION

The invention is illustrated in its application to a prostate biopsy. This application is, of course, not limiting. Furthermore, the invention is illustrated in its application to a needle holder. This application is also not limiting.

Figure 1:
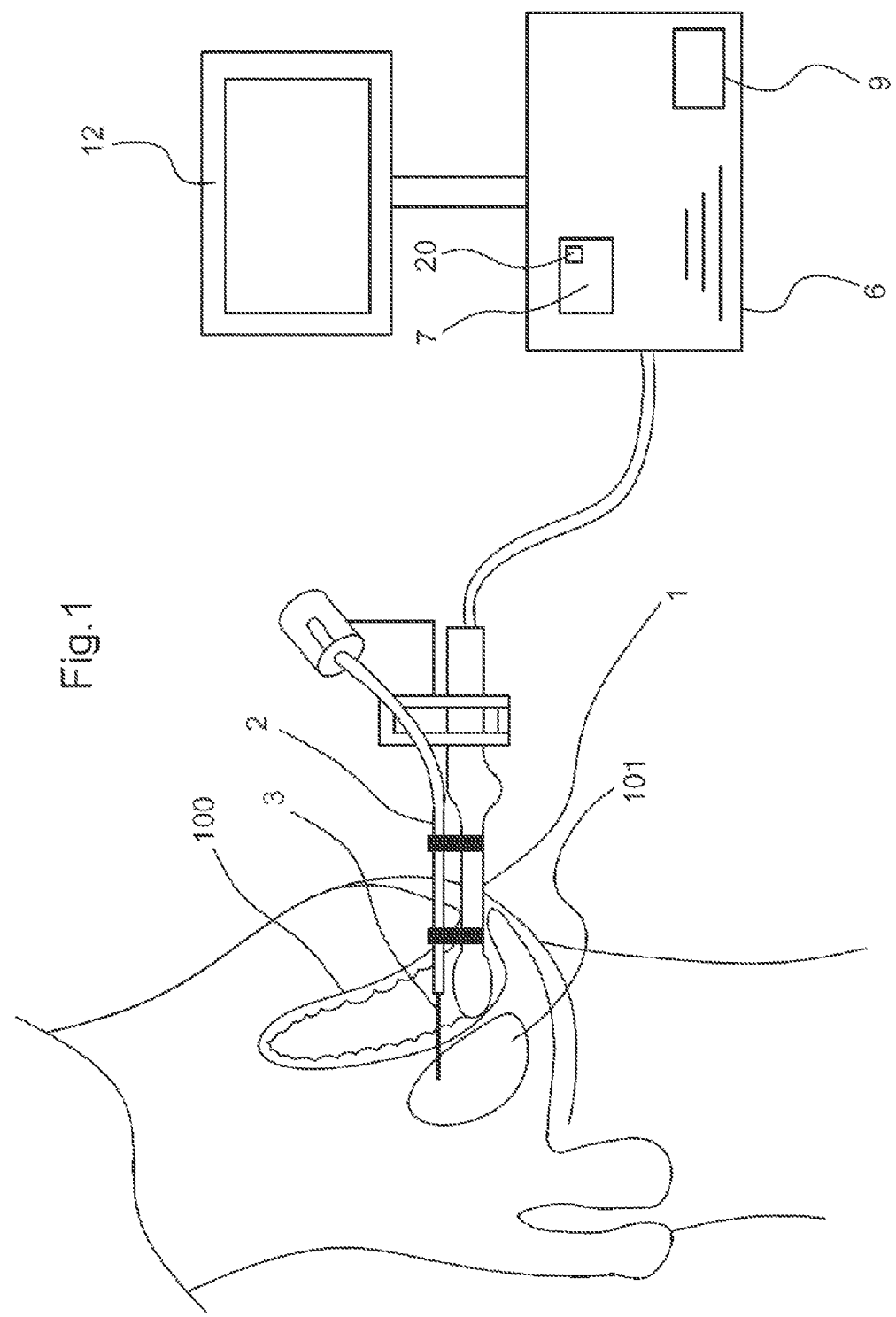
FIG. 1 is a schematic view of a guide device according to the invention, partly inserted into the body of a patient.

Referring to FIG. 1, the guide device according to the invention comprises a medical imaging probe 1, which is illustrated as being inserted into the rectum 100 of a patient. Here, the guide device is intended to guide the probe 1 in proximity to the prostate 101 of the patient. The probe 1 comprises means for acquiring images of the prostate 101.

According to one particular embodiment, the probe 1 is rigidly connected to a medical instrument, here comprising a needle holder 2 for carrying out a biopsy of the prostate 101. The needle holder 2 holds a needle 3. Since the probe 1 is fixed to the needle holder 2, the position of the probe 1 relative to the needle holder 2 is known.

The guide device comprises a control unit 6, to which the probe 1 is connected.

Preferably, the device of the invention comprises a screen 12 for displaying the images acquired by the probe 1. The display screen 12 is connected to the control unit 6. Thus, a practitioner can view the images taken of the prostate 101, or of a particular region of the prostate 101.

According to a preferred embodiment, the control unit 6 comprises means 9 for storing the images acquired by the probe.

Figure 2:
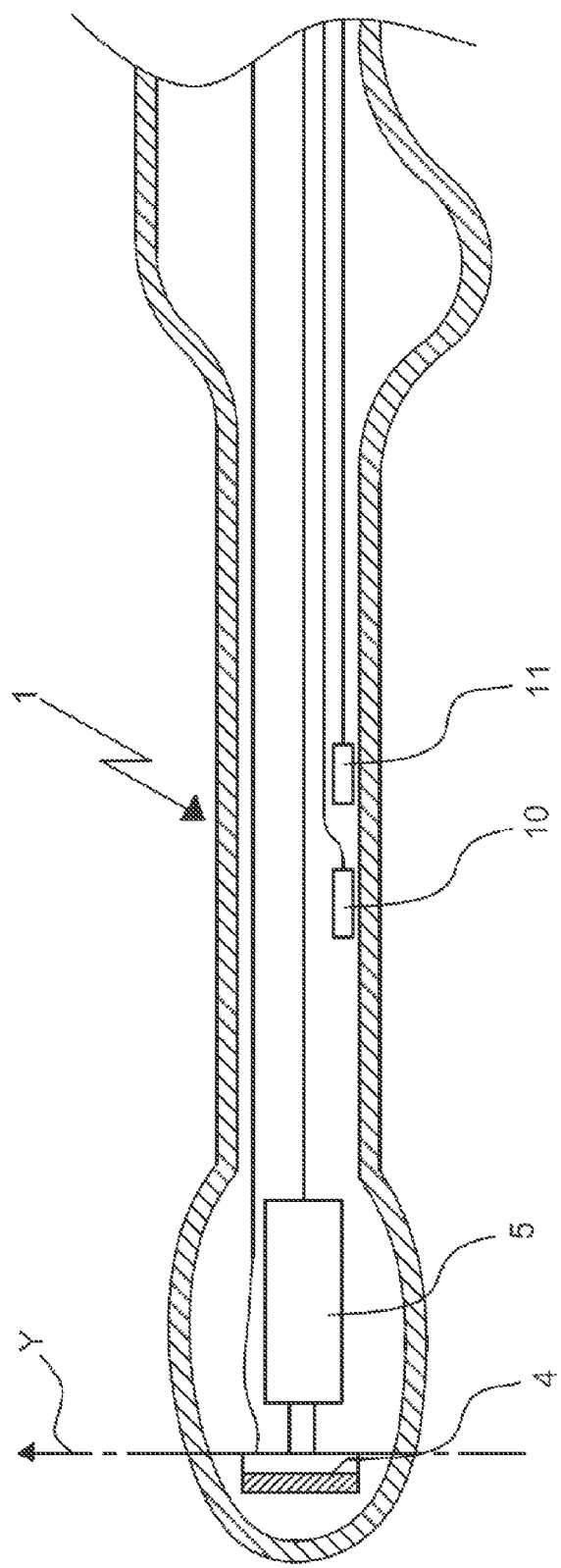
FIG. 2 is an enlarged view in section of a part of the guide device illustrated in FIG. 1.

Referring to FIG. 2, according to a preferred embodiment, the acquisition means comprise a linear ultrasound array 4 for acquiring images in two dimensions. The acquisition means furthermore comprise in this case a motor 5 which is arranged in the probe 1 so that rotation of the axis of the motor 5 causes rotation of the linear ultrasound array 4 about a first axis Y.

Preferably, the motor 5 is a stepper motor, which makes it possible to displace the linear ultrasound array 4 precisely because there is no accumulation of an error. The images acquired by the linear ultrasound array 4 are therefore of better quality. Furthermore, the motor 5 can thus bring the linear ultrasound array 4 into a precise position, even over a small range of rotation angle about the first axis Y.

The motor 5 and the linear ultrasound array 4 are connected to the control unit 6, for example by wires.

According to a preferred embodiment, the control unit 6 controls the motor 5 and the linear ultrasound array so that the motor 5 moves the linear ultrasound array 4 in a restricted rotation range about the first axis Y, typically in a rotation range of 20°, when the linear ultrasound array 4 is acquiring images.

Preferably, the control unit 6 controls the motor 5 and the linear ultrasound array 4 so that the linear ultrasound array 4 acquires a small number of images, typically three images, when it is rotated by the motor 5. Preferably, the linear ultrasound array 4 acquires the images at rotation angles distributed regularly over the rotation range about the first axis Y.

According to a preferred embodiment, the control unit 6 controls the motor 5 and the linear ultrasound array 4 so that the motor 5 brings the linear ultrasound array into an initial position, referred to as the reference position, and locks the linear ultrasound array 4 in this reference position for the time taken for the linear ultrasound array 4 to acquire at least one image. The motor 5 then drives the linear ultrasound array 4 in rotation over a rotation range centered around this reference position, the linear ultrasound array 4 acquiring other images during this rotation. Even more preferably, the motor 5 is controlled so as to lock the linear ultrasound array 4 in each predetermined position in which the linear ultrasound array 4 is meant to acquire an image, for the time taken for the linear ultrasound array to acquire said image.

According to a preferred embodiment, the control unit 6 controls the motor 5 and the linear ultrasound array 4 so that, after a first series of image acquisitions, the motor 5 brings the linear ultrasound array 4 into an initial position for a second series of image acquisitions, said initial position being determined at least on the basis of the images of the first series.

Thus, the images of the second series are acquired for very particular positions of the linear ultrasound array 4, in order to focus information collection on a region of the prostate 101 to be studied in more detail, which region is identified with the aid of the first series of images. This makes it possible, in particular, to maximize a quality of localization of the probe 1 relative to said region.

According to the invention, the control unit 6 comprises means 7 for processing the images acquired by the image acquisition means.

Furthermore, the device comprises at least one first sensor 10 fixed to the probe 1 and capable of generating signals which can be used by the processing means 7 in order to deduce therefrom at least one rotation of the probe 1 in space. The first sensor 10 is, for example, connected to the control unit 6 by wires. Preferably, the first sensor 10 comprises at least one gyroscope generating usable signals which make it possible to calculate an angular position of the probe 1 in space.

Thus, on the basis of the signals generated by the first sensor 10, the rotation of the probe 1 in space is determined in real time. In this way, the determination of the position of the probe 1 relative to the prostate 101, and therefore in this case of the needle holder 2 relative to the prostate 101, is speeded up. Since the prostate 101 has only little rotational movement of its own, mere knowledge of the rotation of the probe 1 in space makes it possible to estimate in an already precise manner the position of the probe 1 relative to the prostate 101.

Furthermore, the processing means 7 comprise means 20 for estimating plausible positions of the probe 1, making it possible to calculate a set of plausible positions of the probe with respect to the prostate on the basis of the angular position of the probe 1 in space, that is to say on the basis of a partially known position of the probe in space.

Subsequently, on the basis of a reference image and the processing of the images acquired by the acquisition means and the plausible positions of the probe 1 in space, the processing means 7 determine during operation the position of the probe 1 relative to the prostate 101. Once the position of the probe 1 relative to the needle holder 2 is known, the processing means 7 in this case also make it possible to determine the position of the needle holder 2 relative to the prostate 101.

Referring to FIG. 3, according to a particular embodiment, the position of the probe 1 relative to the prostate 101 is determined as follows.

During an initialization sequence, in a first step 201, the acquisition means acquire a first image, referred to as the reference image $I_r$, and transmit it to the processing means 7. The reference image is for example an overall image of the prostate 101, or alternatively an image of a particular region of the prostate 101. At the same time, the first sensor 10 generates signals which can be used to determine an angular position of the probe 1 in real time. Preferably, the processing means 7 determine in real time the L angular positions $A_l$ of the probe 1 during the time which the acquisition of the reference image $I_r$ has taken. In a second step 202, on the basis of the L angular positions $A_l$ determined in the first step 201, the processing means 7 calculate the average angular position $A_r$ of the probe 1 by the following formula:

$$A_r = (1/L)\Sigma A_l$$

In a third step 203, the processing means 7 store the reference image $I_r$ as well as the average angular position $A_r$ f the probe 1, associated with this reference image $I_r$.

During a sequence of moving the probe 1, in a first step 301, the acquisition means acquire at least one image $I_s$ and transmit it to the processing means 7. At the same time, the first sensor 10 generates signals which can be used to determine an angular position of the probe 1 in real time.

Preferably, the processing means 7 determine in real time the L angular positions $A_l$ of the probe 1 during the time which the acquisition of the image $I_s$ has taken. In a second step 302, on the basis of the L angular positions $A_l$ determined in the first step 301, the processing means 7 calculate the average angular position $A_s$ of the probe 1 by the following formula:

$$A_s = (1/L)\Sigma A_l$$

During a third step 303, the processing means 7 determine the relative angular position A of the probe by the formula:

$$A = (A_s)^{-1} A_r$$

It should be recalled that $A_r$ is the average angular position of reference of the probe 1 and $A_s$ is the average angular position of the probe 1, associated with the sequence of moving the probe 1.

During a fourth step 304, the estimation means 20 implement the following algorithm.

For each integer m between 1 and M, M being an integer predetermined, for example, by a statistical analysis of data of a plurality of initial tests, the estimation means 20 determine $T_m$ a plausible position of the probe 1 relative to the prostate 101 by the following formula:

$$T_m = \text{Mod}(A, m)$$

where Mod is a statistical or cinematic model describing a restricted number of plausible positions of the probe 1 with respect to the prostate 101 on the basis of the reference image Ir.

For example, Mod(A,m) may define regular translational sampling for a given orientation by the following formula:

$$\text{Mod}(A, m) = \begin{cases} t_x = (m \bmod x) * S_x - x_0 \\ t_y = ((m/x) \bmod y) * S_y - y_0 \\ t_z = m/(x*y) * S_z - z_0 \end{cases}$$

so that the position $T_m$ is then defined by $$T_m(x,y,z) = A(x,y,z) + (t_x\ t_y\ t_z)^T$$

$x_0$, $y_0$, $z_0$ defining the center of the sampling region, $S_x$, $S_y$, $S_z$ defining the scaling of the sampling region.

The parameters x, y, z; $S_x$, $S_y$, $S_z$ and $x_0$, $y_0$, $z_0$ are, for example, determined by a statistical analysis.

The processing means 7 then evaluate a similarity parameter $S_m$ between the image $I_s$ acquired at the start of the movement sequence and the reference image $I_r$ transformed on the basis of the position $T_m$ according to the formula:

$$S_m = \text{Sim}(I_s, I_r \cdot T_m)$$

where Sim is a measurement function of the distance between two images or two subsets of images. Sim is, for example, a measurement function of the cross-correlation of two images (or of two subsets of images) which is determined over the gray levels of the images (or of the elements of the two subsets of images).

Thus, during the fourth step 304, on the basis of the information about the rotation of the probe 1 in space and a statistical or cinematic model Mod, the estimation means 20 predict a limited but sufficiently exhaustive number of plausible positions of the probe 1 relative to the prostate 101. For each plausible position, the processing means 7 also estimate a similarity parameter between the image acquired at the start of the movement sequence and a transformation of the reference image on the basis of the associated plausible position. Thus, a similarity parameter $S_m$ is associated with each plausible position $T_m$.

During a fifth step 305, the processing means 7 implement the following algorithm.

For each integer n between 1 and N, N being an integer predetermined by a statistical analysis of data of a plurality of initial tests, the processing means 7 determine the similarity parameter $S_j$ corresponding to the $n^{th}$ best result in the list of similarity parameters $\{S_1, \ldots, S_m\}$ calculated during the fourth step 304.

The processing means 7 then carry out a local optimization on the chosen similarity parameter $S_j$ by varying the associated position $T_j$ until a maximum similarity parameter $S_n$ is found for a position $T_n$ which lies in the vicinity of $T_j$. The processing means use, for example, the following formula:

$$\langle S_n, T_n=T_j\cdot T_{max}\rangle = \arg\max_{T[T_j]} \mathrm{Sim}(I_s, I_r \cdot T_j \cdot T)$$

where T is the optimization variable (the position T is varied in order to find, around $T_j$, a position $T_{max}$ which maximizes the similarity).

Local optimization techniques such as the conjugate gradient descent method or Powell-Brent method are well known in the prior art and may be used for local optimization on the aforementioned similarity parameter $S_j$.

Thus, during the fifth step 305, the processing means 7 test and classify the plausible positions $T_m$ of the probe 1 relative to the prostate 101 which were calculated during the fourth step 304. The positions $T_m$ associated with a maximum similarity parameter are chosen as candidates which have a high probability of being close to the real position of the probe 1 with respect to the prostate 101. These positions with a maximum similarity parameter are then studied in more detail by carrying out a local optimization on the similarity parameter for each position with a chosen maximum similarity parameter.

Thus, only certain positions $T_m$ provided by the estimation means are selected in order to reduce the number of minimizations carried out during the local optimization.

Next, during a sixth step 306, the processing means 7 determine the maximum similarity parameter $S_k$ among all the similarity parameters determined during the fifth step 305. The position $T_k$ associated with this maximum similarity parameter $S_k$ is the position of the probe 1 determined with respect to the prostate 101. This position $T_k$ is used, for example, in order to guide the probe 1 relative to the prostate 101.

The image processing consists here of the combination of a calculation of similarity between images with local optimization (based, for example, on the Powell-Brent or gradient descent method). The optimization step consists in starting from one or more initial positions and varying it or them until the similarity between the two images to be anatomically superimposed is locally maximum.

Referring to FIG. 2, according to a preferred embodiment, the device comprises a second sensor 11, which is fixed to the probe 1 and capable of generating signals which can be used by the processing means 7 in order also to deduce a translation of the probe 1 in space therefrom.

On the basis of the signals generated by the first sensor 10 and the second sensor 11, the rotation and the translation of the probe 1 in space are determined in real time, which speeds up even further the determination of the position of the probe 1, and therefore of the needle holder 2, relative to the prostate 101 once an image has been acquired.

The first sensor 10 and the second sensor 11 are compact and make it possible to simplify considerably the calculations by the processing means 7.

The device according to the invention makes it possible to know precisely and rapidly the position of the probe relative to the anatomical volume while obviating a bulky system of the transmitter/receiver type of the prior art, and to do so despite the possible movements of the anatomical volume. The device thus makes it possible to guide the probe precisely and rapidly relative to the anatomical volume, but also here to guide the instrument precisely and rapidly relative to the anatomical volume. Advantageously, the sensor or sensors fixed to the probe are lightweight, of small dimensions, and are arranged in or on the probe.

The device may furthermore be used for numerous applications. For example, a practitioner may move the probe and/or the instrument by himself while being assisted by the images acquired by the probe and the relative position of the probe and the instrument with respect to the anatomical volume, in order to guide the probe and/or the instrument. As a variant, the device may comprise means for moving the probe and/or the instrument, the movement means comprising for example an articulated arm. The control unit will generate control instructions intended for the movement means in order to control at least one movement of the probe and/or of the instrument relative to the anatomical volume on the basis of the images acquired by the probe and the position of the probe relative to the anatomical volume. As a variant, the movement means will be jointly manipulable with the practitioner.

The invention is not limited to that which has been described above, but rather includes any variant falling within the scope defined by the claims.

Although the invention is illustrated in an application to a prostate biopsy, the invention may be used in other applications. For example, the invention may allow treatment of a disease of the prostate, in which case an instrument associated with the probe is brought up to the prostate through the perineum or the rectum. The invention may allow puncture of an anatomical volume of the female genital system, for example puncture of the uterus, in which case an instrument associated with the probe is brought up to the anatomical volume through the vagina. The invention may also allow puncture of another anatomical volume such as the kidney, spine, a breast, a lung, etc.

If the probe is intended to be inserted into the body of the patient in order to reach the intended anatomical volume, the probe may be introduced through a natural passage such as the rectum, but also through an artificial passage. The probe may also be guided relative to the intended anatomical volume without being inserted into the body of the patient, depending on the application for which the invention is intended. In any event, the invention is entirely independent of the point of entry of the natural or artificial passage chosen.

The probe may approach any other anatomical volume than a prostate, such as a kidney, a breast, or the Douglas' cul-de-sac, etc. The probe may thus be associated with an instrument other than a needle holder, for example a scalpel, a clamp, a heat probe or an optical fiber, etc. The probe may also not be associated with another instrument, in which case the invention makes it possible to study a particular region of an anatomical volume via the probe. In the case in which the device comprises a medical instrument, the medical instrument may be not rigidly connected to the probe. The device will then comprise means for localizing the medical instrument relative to the probe, so that the processing means determining the position of the probe relative to the anatomical volume can also determine the position of the instrument relative to the anatomical volume. The device according to the invention will thus make it possible to guide the instrument relative to the anatomical volume. For example, the means for localizing the medical instrument relative to the probe will comprise mechanical means for fixing the medical instrument to the probe, such as an articulated arm.

The probe may comprise a different number of sensors and other types of sensor. Thus, the probe may comprise only one sensor making it possible to deduce the rotation of the probe in space, this being the most important information. The translational movements of the probe in space will then need to be determined in a traditional way by processing the images acquired by the acquisition means. The first sensor may, for example, comprise at least one inclinometer and/or at least one accelerometer and/or at least one gyrometer. The sensors may be fixed to the probe without being arranged inside the probe.

The image acquisition means may be other than those described. For example, the image acquisition means may be of an optical rather than ultrasound type. For example, the acquisition means may comprise two linear ultrasound arrays arranged in the probe so as to cross over orthogonally, but will not have a motor. The device may not comprise a screen for displaying the images taken by the probe. Preferably, the device will comprise an interface for communication with a person using said device, such as a display screen and/or audio communication means and/or haptic feedback means.

Although it has been indicated that the control unit was arranged so as to control the motor and the linear ultrasound array so that, in use, after a first series of image acquisitions, the motor brings the linear ultrasound array into an initial position for a second series of image acquisitions, said initial position being determined at least on the basis of the images of the first series, the control unit may not comprise such a function. For certain interventions, it is sometimes necessary for an image illustrating at least a part of the reference volume with at least a part of the medical instrument associated with the probe to be always acquired during a series of image acquisitions. Such an image is in fact very useful for the clinician to orientate himself. Under these conditions, the initial position for the second series of image acquisitions must also be determined so that such an image is acquired during the second series.

The method for determining the position of the probe may be different to that presented. Only one angular position of the probe may be determined, rather than an average angular position of the probe. Other image processing steps may be added in order to refine the determination of the position of the probe 1 relative to the prostate 101. The integers N and M may be determined during the initialization sequence. For example, the processing means 7 may continue the image processing after the step of determining Tk, for example by estimating residual transformations such as the deformations of the prostate 101 caused by the probe 1.

As a variant, the method may comprise an additional step of validating the result of the calculation of the position of the probe relative to the anatomical volume. This step consists, for example, in calculating a complex measure of similarity between the reference image transformed by the calculated position of the probe relative to the anatomical volume and the image acquired by the acquisition means, and of validating this similarity for example by a threshold method. This will make it possible to identify an erroneous calculation of the position of the probe relative to the anatomical volume and optionally to warn the user or suggest to him new strategies for localizing the probe relative to the anatomical volume.

The statistical or cinematic model implemented by the estimation means may thus be different to that described. The statistical or cinematic model may thus be specific to the type of intervention intended, or even specific to the type of category to which the patient belongs. The model may thus be a cinematic model of plausible shifts of the probe during transrectal access to the prostate, such as that described in Patent Application FR 2 920 961 A1, a statistical model of the principal component analysis (PCA) type, which makes it possible to describe the principal axes of variation and the extent of the variations on the basis of a statistical analysis, a model constructed according to Bayes' laws intended to identify positions of the probe relative to the anatomical volume with a posteriori maximum probabilities by considering the signals generated by the sensor fixed to the probe. The model in question will in general be constructed on the basis of a statistically sufficient number of representative clinical cases. As a variant, the estimation means will comprise calculation means which will provide regular subsampling of the axes of the transformations space fixed to the probe in space, these not being covered by the signals of the sensor fixed to the probe and/or having a high probability of being exposed to the shift of the anatomical volume.

The similarity calculation steps may be implemented on the basis of a correlation coefficient (CC) or the sum of absolute distances (SAD).

The invention claimed is:

1. A device for guiding a medical imaging probe in order to bring said probe in proximity to an anatomical volume, the probe comprising means for acquiring images of the anatomical volume, the device comprising at least one sensor fixed to the probe and capable of generating signals representing at least one rotation of the probe in space, the device comprises a control unit which is connected to the probe and comprises means for processing the images in order to localize the probe relative to the anatomical volume, the processing means being capable of deducing a rotation of the probe in space on the basis of the signals generated by the sensor, the processing means comprising means for estimating a plurality of plausible positions of the probe relative to the anatomical volume on the basis of at least the deduction of the rotation of the probe in space, the processing means being arranged in order to determine the position of the probe relative to the anatomical volume on the basis of:
   a reference image of the anatomical volume acquired by the means for acquiring images of the anatomical volume during an initialization phase,
   at least one image acquired by the image acquisition means during a phase of motion following the initialization phase, and
   the plausible positions.

2. The device as claimed in claim 1, wherein the sensor is capable of generating only signals representing the rotation of the probe in space.

3. The device as claimed in claim 1, wherein the processing means are arranged in order to determine only an angular position of the probe relative to the anatomical volume on the basis of the signals generated by the sensor, and the estimation means are arranged in order to determine a plurality of plausible positions of the probe on the basis of said angular position.

4. The device as claimed in claim 1, wherein the image acquisition means comprise a linear ultrasound array, and a motor which is arranged so as to drive the linear ultrasound array in rotation about a rotation axis during use.

5. The device as claimed in claim 4, wherein the control unit is arranged so as to control the motor and the linear ultrasound array so that the motor moves the linear ultrasound array in a restricted rotation range, typically of 20 degrees, about the rotation axis during use.

6. The device as claimed in claim 4, wherein the control unit is arranged so as to control the motor and the linear ultrasound array so that during use, after a first series of image acquisitions, the motor brings the linear ultrasound array into an initial position for a second series of image acquisitions, said initial position being determined at least on the basis of the images of the first series.

7. A method for guiding a medical probe for medical imaging in order to bring the probe in proximity to an anatomical volume; the method comprising:
providing a probe that acquires images of the anatomical volume, wherein fixed to the probe is at least one sensor capable of generating signals representing at least one rotation of the probe in space and performing the following steps:
acquiring a reference image of the anatomical volume during an initialization phase and during a phase of motion following the initialization phase;
processing the signals generated by the sensor in order to deduce therefrom at least one rotation of the probe in space;
estimating a plurality of plausible positions of the probe relative to the anatomical volume on the basis of at least the deduction of the rotation of the probe in space;
processing the images in order to localize the probe relative to the anatomical volume by determining the position of the probe relative to the anatomical volume on the basis of the reference image of the anatomical volume, of at least one image acquired by the probe, and of the plausible positions which have been determined.

8. The method as claimed in claim 7, wherein the step of estimating a plurality of plausible positions is carried out by a statistical or cinematic model.

9. The method as claimed in claim 7, wherein the step of estimating a plurality of plausible positions is carried out on the basis of the deduction of only the rotation of the probe in space.

10. The method as claimed in claim 7, furthermore comprising the step of selecting only certain plausible positions of the probe relative to the anatomical volume in order to initialize the step of processing the images, in order to localize the probe relative to the anatomical volume by determining the position of the probe relative to the anatomical volume.

11. The method as claimed in claim 7, furthermore comprising the step of validating the position of the probe which has been determined relative to the anatomical volume.

12. The method as claimed in claim 7, comprising the successive steps of:
acquiring at least one reference image of the anatomical volume and determining at least one angular position of the probe in space, associated with the reference image, referred to as a reference angular position;
acquiring at least a first image of the anatomical volume and determining at least a first angular position of the probe in space, associated with said image by processing the signals generated by the sensor in order to deduce therefrom the rotation of the probe in space:
on the basis of the reference image, the reference angular position, the first image and the first angular position, determining a finite number of positions of the probe relative to the anatomical volume by a statistical or cinematic model, so as to estimate a plurality of plausible positions of the probe relative to the anatomical volume;
for each plausible position, calculating a similarity parameter between the image of the anatomical volume and a transformation of the reference image on the basis of said plausible position;
with the aid of the similarity parameters calculated in the preceding step, selecting among the plausible positions closest to a real position of the probe relative to the anatomical volume;
refining the determination of each position of the probe relative to the anatomical volume by local optimization on each of the similarity parameters associated with the positions;
among all the positions thus refined, selecting the position whose associated similarity parameter is maximum after the local optimization step, said position being the position determined for the probe relative to the anatomical volume.

13. The method as claimed in claim 12, wherein the similarity parameter is calculated on the basis of a cross-correlation over the gray levels between the image of the anatomical volume and the transformation of the reference image.

14. A medical device, comprising:
an imaging probe configured to acquire images of an anatomical volume;
a device configured to guide the imaging probe in order to bring the probe in proximity to the anatomical volume;
the device comprising at least one sensor fixed to the imaging probe and that generates a signal representing at least one rotation of the probe in space; the device comprises a control unit connected to the probe and a processor in which the images are processed in order to localize the probe relative to the anatomical volume, the processor configured to deduce a rotation of the probe in space on the basis of the signals generated by the sensor and configured to estimate a plurality of plausible positions of the probe relative to the anatomical volume on the basis of at least the deduction of the rotation of the probe in space, and the processor arranged to determine the position of the probe relative to the anatomical volume on the basis of a reference image of the anatomical volume acquired by the imaging probe during an initialization phase, of at least one image acquired by the imaging probe during a phase of motion following the initialization phase, and the plausible positions.

* * * * *